United States Patent
Bordewick et al.

(10) Patent No.: US 7,814,911 B2
(45) Date of Patent: Oct. 19, 2010

(54) NARES SEAL

(75) Inventors: Steven S. Bordewick, North Shoreview, MN (US); Laurel D. Brandt, Eagan, MN (US); Mark J. Weimholt, Coon Rapids, MN (US)

(73) Assignee: AEIOMed, Inc., Minneapolis, MN (US)

( * ) Notice: Subject to any disclaimer, the term of this patent is extended or adjusted under 35 U.S.C. 154(b) by 890 days.

(21) Appl. No.: 11/097,536

(22) Filed: Apr. 2, 2005

(65) Prior Publication Data

US 2006/0081250 A1    Apr. 20, 2006

Related U.S. Application Data

(60) Provisional application No. 60/619,426, filed on Oct. 15, 2004.

(51) Int. Cl.
- *A62B 18/02* (2006.01)
- *A62B 18/08* (2006.01)
- *A62B 18/00* (2006.01)
- *A61M 15/08* (2006.01)

(52) U.S. Cl. ............... 128/207.13; 128/207.18; 128/207.11; 128/206.21; 128/206.27; 128/200.24

(58) Field of Classification Search ........... 128/200.24, 128/201.22, 203.22, 204.12, 206.11, 206.16, 128/206.23, 207.11, 207.13, 207.18, 206.18, 128/206.29, 206.27

See application file for complete search history.

(56) References Cited

U.S. PATENT DOCUMENTS

| | | | | |
|---|---|---|---|---|
| 853,439 | A * | 5/1907 | Clark ................... | 128/207.18 |
| 2,245,969 | A * | 6/1941 | Francisco et al. ...... | 128/207.18 |
| 4,782,832 | A | 11/1988 | Trimble et al. | |
| 4,919,128 | A | 4/1990 | Kopala et al. | |
| 4,944,310 | A | 7/1990 | Sullivan et al. | |
| 5,042,478 | A * | 8/1991 | Kopala et al. .......... | 128/207.18 |
| 5,477,852 | A * | 12/1995 | Landis et al. .......... | 128/207.18 |
| 5,687,715 | A * | 11/1997 | Landis et al. .......... | 128/207.18 |
| 5,752,511 | A * | 5/1998 | Simmons et al. ....... | 128/207.18 |
| 6,093,169 | A * | 7/2000 | Cardoso ................. | 604/94.01 |
| 6,347,631 | B1 | 2/2002 | Hansen et al. | |
| 6,412,487 | B1 | 7/2002 | Gunararatnan et al. | |
| 6,418,928 | B1 | 7/2002 | Bordewick et al. | |
| 6,463,931 | B1 | 10/2002 | Kwok et al. | |
| 6,513,526 | B2 | 2/2003 | Kwok et al. | |
| 6,516,802 | B2 | 2/2003 | Hansen et al. | |
| 6,530,373 | B1 | 3/2003 | Patron | |
| 6,581,594 | B1 | 6/2003 | Drew | |

(Continued)

*Primary Examiner*—Justine R Yu
*Assistant Examiner*—Annette F Dixon
(74) *Attorney, Agent, or Firm*—Clise, Billion & Cyr, P.A.; Richard Billion

(57) ABSTRACT

Apparatus for providing positive pressure for treatment of snoring and sleep apnea are disclosed. The apparatus includes a nares seal configured to engage the nares of a patient and to direct pressurized air into the airways of the patient. The nares seal can include first and second laterally spaced delivery tubes defining a generally triangular open space between them. The delivery tubes can extend downward below the nose of a patient and curve inward and upward under the nose of the patient. A first and a second nostril tube are connected to the delivery tubes for insertion into the nares of the patient. A wire support may be provided in each of the laterally spaced delivery tubes. The nares seal may be connected to a mask support of headgear configured to be secured to the head of the patient.

11 Claims, 7 Drawing Sheets

U.S. PATENT DOCUMENTS

| | | |
|---|---|---|
| 6,584,977 B1 | 7/2003 | Scrowski |
| 6,669,712 B1 * | 12/2003 | Cardoso .................... 606/199 |
| 6,679,265 B2 | 1/2004 | Strickland et al. |
| 6,712,072 B1 * | 3/2004 | Lang .................... 128/206.27 |
| 6,854,465 B2 | 2/2005 | Bordewick et al. |
| 6,863,069 B2 | 3/2005 | Wood |
| 7,021,312 B2 * | 4/2006 | Cannon .................. 128/206.29 |
| 2003/0079749 A1 | 5/2003 | Strickland et al. |
| 2006/0005840 A1 * | 1/2006 | Cannon .................. 128/207.11 |

* cited by examiner

NARES SEAL

RELATED APPLICATION

This application claims priority of U.S. Provisional Patent Application No. 60/619,426 filed Oct. 15, 2004.

FIELD OF THE INVENTION

This invention relates generally to a nasal mask, and in particular to a nares seal, for providing pressurized gas to a patient during treatment by continuous positive airway pressure (CPAP). The pressurized gas may be ambient air, oxygen or a mixture thereof.

BACKGROUND

Sullivan et al. disclosed treating sleep apnea by continuous positive airway pressure (CPAP) at 4.5-10 cm water applied to a patient by way of the nose, and reported that the applied pressure completely prevented upper airway occlusion during sleep, see U.S. Pat. No. 4,944,310. Apparatus that was fitted to the face of a patient, which is now sometimes referred to as a patient interface, included headgear in the form of an open cap formed by a headband for fitting around the head and by a pair of cross-bands. A plastic concertina-type flexible air supply line lead downwardly via a first fixing on the headband to one side of the nose to the underside of the nose, and then upwardly away from the nose via a second fixing on the headband to the opposite side of the nose, beyond which the supply line terminated at a variable restriction device for permitting air to escape while providing a positive pressure that may be adjusted to the needs of a particular patient. A rigid tubular nostril piece was fitted in the air supply line at the underside of the nose and could be provided with a pair of soft tubes or so-called "nasal inserts" for fitting into the nares for treatment of difficult patients.

Continuous positive airway pressure has become the system of choice for the treatment of chronic sleep apnea, chronic pulmonary obstruction and snoring. Many systems are now available. These systems include a source of pressurized air, tubing leading the source to the patient and patient/tubing interfaces of various types. All strive to use the lowest possible pressure to maintain airway patency during sleep. To do so, the system must be substantially leakproof, so that the pressurized air enters the patient's airway rather than leaking to atmosphere.

The main choices of patient interface are full nasal masks that surround the nose and masks that have outlets directly into the nares. Each type has its own problems. A full nasal mask is generally made of a rigid material with a flexible "skirt" and must be firmly apposed to the face. Differences in facial topology may make the seal ineffective. Nares masks have an advantage in that the point of contact between the nares, the area of the seal, is much reduced.

Most CPAP assemblies have straps attached to the face or nasal mask that encircle the head in order to supply sufficient apposing force. Applicants' co-pending U.S. patent application Ser. No. 10/643,642, now U.S. Pat. No. 6,854,465 discloses a unique means of applying apposing force via a steel wire that presses the mask to the face of a patient, eliminating the need for straps to pull the mask to the face of the patient.

U.S. Pat. No. 4,782,832 (Trimble) discloses a patient interface that fits to the head by means of an open cap having a circumferential band that fits around the head and a cross-band that passes over the head and is secured to the circumferential band at positions coinciding with but somewhat above the ears. A flexible gas supply hose passes in a posterior-anterior direction to the crown of the head where it is secured to the cross-band, then to the circumferential band to which it is secured, and finally in spaced parallel relationship in front of the nose where it terminates in a plug connector. A nares mask fits via a tubular socket connector to the plug connector at the end of the hose. The socket connector is formed integrally with a plenum chamber of rigid material that fits under the nares and carries a pair of upstanding nares tubes dimensioned and positioned to fit into and seal with the nares of the patient. A pair of straps extend from the circumferential band at locations above the patient's ears obliquely forwardly and downwardly across the patient's cheeks and are attached to opposite sides of the plenum chamber, thereby supporting the plenum chamber in position below the nares. The use of rigid material for the plenum chamber avoids deformation thereof under the loads applied by the diagonal face straps, which in the case of rubber or other deformable material would create significant deformation. Puritan Bennett of Pleasanton, Calif. is currently marketing as the Adam interface system a patient interface having a supply hose, headgear and a nares mask arranged as described above.

U.S. Pat. No. 6,347,631 (Hansen) discloses a device for holding a mask in place over the nose of a patient's head. It comprises an anchor adapted to fit behind the head of a patient about the occipital lobe of that patient and a forward anchor adapted to fit against a corresponding portion of the patient's head at a forward anchoring position which may be at the top of the patient's head or at the patient's forehead. A curved spring connects the occipital anchor and the forward anchor and is alleged to permit them to attach the device to the patient's head, the occipital anchor, spring or other biasing means, and forward anchor being substantially aligned with the medial line of the skull. For improved fixation and increased security side straps may be provided which pass around the sides of the patient's head and connect the occipital anchor with the forward anchor. A mounting member extends from the forward anchor for locating the mask in place over the nose or other orifice. Tubing from a blower is secured along the biasing structure and the mounting member and terminates in a connector to which a nasal mask can be attached. The nares mask is also based on a plenum chamber of rigid material that fits under the nares and carries a pair of upstanding naris tubes dimensioned and positioned to fit into and seal with the nares of the patient. Again, loads between the mask and the face of the patient may be significant, and making the mask predominantly of rigid material avoids deformation under these loads. Puritan Bennett is currently marketing under the trade mark Breeze SleepGear a patient interface having a supply hose, headgear and a nasal mask arranged as described above.

US Published Application 20030079749 (Strickland) discloses a nasal mask comprising first and second nasal inserts for insertion into a patient's nares, a left and right delivery tube coupled to both of said nasal inserts so that each nasal insert communicates with both the left delivery tube and right delivery tube, and a coupler located remote from said nasal inserts for coupling said mask to a source of respiration gas. The left and right delivery tubes pass downward to below the chin, where the coupler joins a tube leading from a blower. The nasal mask is supported on the head by a strap that is attached to one delivery tube, passes behind the head and is then attached to the other delivery tube.

Although CPAP units and masks are available as explained above, many patients who would benefit from CPAP fail to use their units regularly. The tight fit necessary for an air seal plus the bulkiness of the unit cause a feeling of claustrophobia and the unit is soon left unused.

It is an object of the invention to provide a further nasal mask, embodiments of which may be inexpensive to manufacture, easy to adjust, and comfortable, unobtrusive and stable to wear.

SUMMARY OF THE INVENTION

The invention provides a nares seal comprising:

a connector having an air orifice formed therethrough;

first and second laterally spaced delivery tubes connecting with said air orifice and defining between them a generally triangular open space which extends, when in use, downwardly to a point below the nose of a patient, said delivery tubes thence curving inwardly and upwardly to approach the nose of a patient;

first and second nostril tubes connected with said delivery tubes for insertion into the nares of a patient; and wire support for said laterally spaced tubes extending from the connector to about where said tubes curve inwardly and upwardly.

The invention also provides a nares seal comprising an air orifice surrounded by a connector; two laterally spaced outlet tubes defining a triangular open space and extending downward to a point below the nose of a patient and thence curving upward and inward to approach the nares of a patient; a flange at the end of the outlet tubes; and a wire support attached to the outlet tubes and extending to the upward curve of the outlet tubes.

The invention further provides apparatus for fitting to the head of a patient for supply of gas to the nose at a positive pressure for treatment of snoring and sleep apnea, said apparatus comprising:

headgear for fitting to the head of a patient;

a mask support forming part of said headgear and held in use by portions of said headgear in a stable position above the nose of the patient, said mask support including a manifold chamber, a first connector opening above said manifold chamber for attachment of a gas supply line and a second connector depending from said manifold chamber; and a nares seal connected to said second connector by a third connector forming part of said seal and having an air orifice formed therethrough, said seal further comprising first and second laterally spaced delivery tubes connecting with said air orifice and defining between them a generally triangular open space which extends, when in use, downwardly to a point below the nose of a patient, said delivery tubes thence curving inwardly and upwardly to approach the nose of a patient, first and second nostril tubes connected with said delivery tubes for insertion into the nares of a patient; and wire support for said laterally spaced tubes extending from the connector to about where said tubes curve inwardly and upwardly. The above apparatus may further comprise a blower for feeding air into the gas supply line.

BRIEF DESCRIPTION OF PREFERRED FEATURES

In the preferred embodiment, the lateral outlet tubes are joined in a collar before curving backward and up to the nares. In other embodiments, the outlet tubes may remain separated and insert independently into the nares of a patient.

The connector is advantageously a molding of rigid plastics material that fits at an upper end of a body of said mask, said body being a one-piece molding of a deformable plastics or rubber material, e.g. silicone rubber.

The wire support may be a single wire of a generally inverted U-shape, said wire being rigidly attached at the apex of the inverted U to said connector and the limbs of the wire support being embedded in the plastics material of said delivery tubes. Preferably said limbs of said wire support are embedded at the anterior of said delivery tubes, e.g. in ribs formed along the anterior of said delivery tubes and upstanding therefrom.

For effective sealing to the anterior nares, the nostril tubes are preferably flanged partway along their length. Advantageously said flange is bounded by upper and lower generally frustoconical surfaces, the upper frustoconical surfaces providing abustments for limiting entry of said tubes into the anterior nares and leading to reduced diameter distal regions for entry into the nares, and the lower frustoconical surfaces being of lesser thickness than the remainder of the nostril tube, whereby deformation of the nostril tube in use occurs preferentially at said lower flange. In some embodiments, said delivery tubes lead to a generally U-shaped transversely directed collar that in use fits below the nose, said nasal tubes being carried by said collar and facing obliquely rearwardly and upwardly therefrom. For best fit into the nostrils, said nostril tubes are oval with their longer dimensions directed inwardly and forwardly as viewed from above, the above layout mimicking the shape of the nose at the nares.

BRIEF DESCRIPTION OF THE DRAWINGS

How the invention may be put into effect will now be described, by way of example only, in the accompanying drawings, in which.

DETAILED DESCRIPTION OF PREFERRED EMBODIMENTS

When used in this application, the following terms have the following meanings:

"Air" is used to denote a gas to be delivered to a patient and includes atmospheric gas, oxygen or a combination thereof.

"Appose" means to press one surface against another.

"Nasal mask" refers to a mask having a pair of nasal tubes that are apposed to the patient at his nostrils or anterior nares for the purpose of delivering air direct into and allowing exhalation direct from the nostrils. A nasal mask may also be apposed to the patient at other points on the patient's face.

"Nares seal" or "seal" refers to a nasal mask that is apposed to a patient only at the nares.

In describing this invention, the outside surface is termed the "front" and is the surface farthest from the face of the patient. The "back" surface is that touching the patient's face. The "top" area or "up" direction is that above the nose of the patient and is the inlet end which connects to an air source and mask support. The "bottom" area or "down" direction that is below the nose of the patient.

The present nares seal finds utility in relation to any cap, harness or other support structure which leads an air supply line to a position above the nose, the air supply line terminating in a connector to which the present nares seal can be removably attached, depending from that connector towards the nose. Thus the seal can be used with CPAP apparatus including a forehead support for a mask provided that the forehead support is held sufficiently firmly that the need for straps passing across the face from behind the head and connected to the mask itself is avoided. Since the body of the present nares seal is of silicone rubber or other deformable material, the attachment of straps to the seal itself is undesirable.

Figure 1:
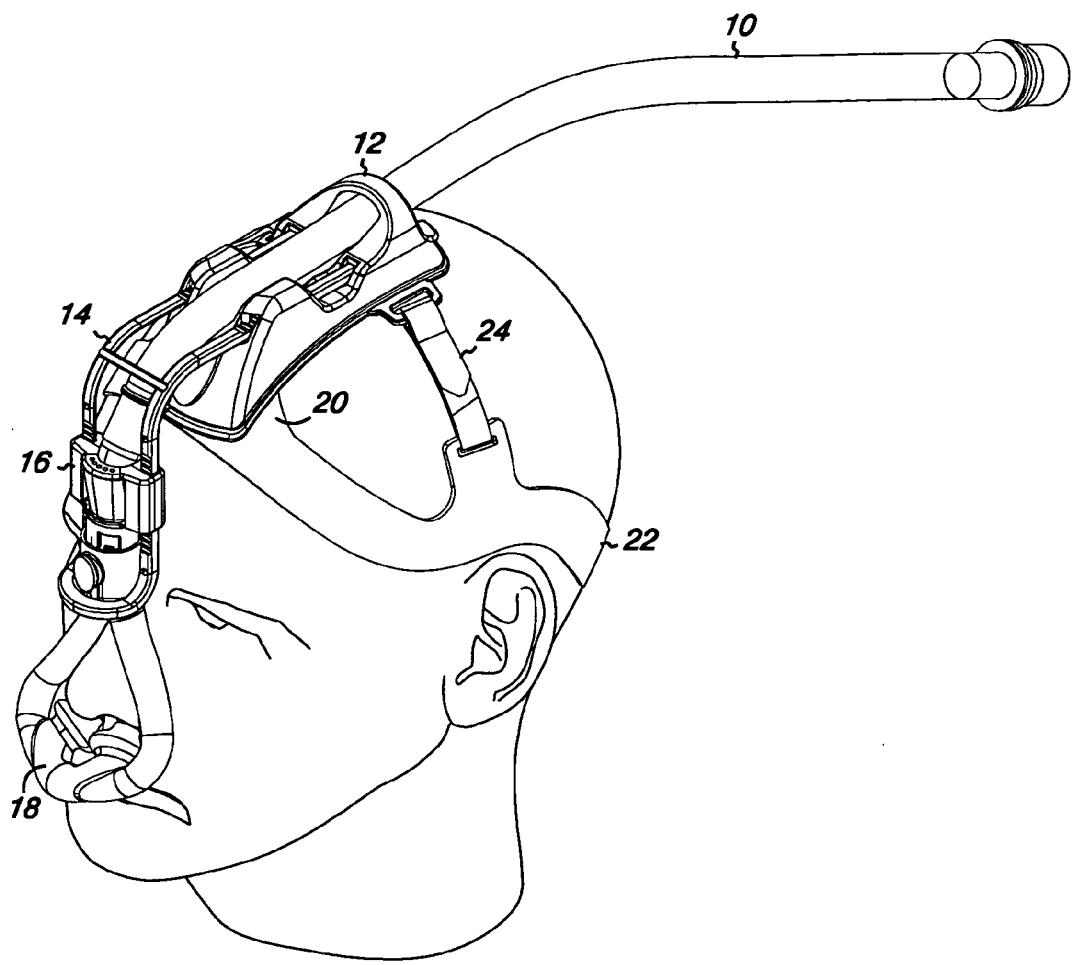
FIG. 1 is a ¾ view of a human head with gas supply apparatus fitted thereto, said gas supply apparatus incorporating an embodiment of a nasal mask according to the invention.

The present nares seal is suitable for use as part of apparatus as shown in FIG. 1 for fitting to the head of a patient for supply of gas to the nose at a positive pressure for treatment of snoring and/or sleep apnea (see also co-pending U.S. Ser. No. 11/056,858, the disclosure of which is incorporated herein by reference). The apparatus of FIG. 1 includes a support 12 of rigid or semi-rigid molded plastics material such as ABS having a length greater than its width and having a concave lower surface profiled so that the support can rest on the top of a human head, directly or via an intermediate layer of deformable material, in a stable attitude facing in an anterior-posterior direction. The support 12 is sized to extend partway across the head and to extend between the top of the head and an upper region of the forehead. Headgear in the form of an open cap for holding the support stably on the head includes a circumferential stabilizing band 22 for fitting around the head between a lower back region of the head and said upper region of the forehead. The cap is also provided with anterior attachment 20 to the support 12, and with lateral attachments to the support 12 via bands 24, thereby holding the support stably on the head when the circumferential band is fitted to the head. A mask holder 14 also of rigid or semi-rigid material e.g. of glass-filled nylon extends forwardly from and is stably carried by the support. The mask holder 14 is sized and shaped to pass clear of the face and of the upper region of the forehead forwardly and downwardly towards the nose. A lower portion of the mask holder 14 is provided with connector carrier 16 which includes a plenum chamber, an upper connector leading to the plenum chamber and facing obliquely rearwards and upwards from the top face of the plenum chamber, and a lower plug connector (not shown) leading from the plenum chamber and facing downwards generally parallel to the vertical direction of the face. A gas supply tube 10 passes via the support 12 and the mask holder 14 to the upper part of the connector carrier 16 where it joins the obliquely facing upper connector. A nares seal 18 for delivering gas at said positive pressure to the nose is attached to the lower plug connector and depends from the connector carrier 16.

A rear upper region of the mask holder 14 is adjustable in an anterior-posterior direction relative to support 12 for adjustably positioning the connector carrier 16 towards and away from the face, for which purpose the mask holder 14 may be toothed to cooperate with a bi-directional clicker or ratchet mechanism (not shown) forming part of the support 12. Thereby the mask holder can be moved to a desired position and is then retained in the selected position until it is positively readjusted. Similarly the connector carrier 16 is adjustable upwardly or downwardly relative to the face on the lower anterior region of mask holder 14 which is also toothed, the connector carrier 16 including a second bi-directional clicker or ratchet mechanism (not shown) by which it can be adjusted to a selected vertical position on the mask holder 14, and is thereafter retained in its selected vertical position until readjusted.

The nares seal 18 has a socket or other connector that is connectable to the plug connector or other depending connector device of the connector carrier 16. The inlet end is attached via the connector to the plenum and thence to a blower or other air source which is external to the nares mask. The mask connector may be of any size to accommodate attachment to any plenum and air supply. Although the mask may be made in a range of sizes for different patients, in a typical size it is of overall height about 105 cm, overall width about 66 cm and internal volume about 20-50 ml, for a wide range of patients conveniently about 30 ml. Its main body is a one-piece molding in medical grade silicone rubber or other resiliently deformable rubber or plastics material and is devoid of openings other than an upper orifice 26 and nares tubes described below. Its internal volume is only a small fraction of the volume of air inhaled or exhaled at each breath, which is typically about 500 ml, so that no apertures for exhaled air need be formed in seal 18. Instead, upwardly facing apertures for escape of excess air flowing from the blower through the hose 10 and for escape of exhaled air can be provided at the connector carrier 16, said apertures opening through the upper surface of connector carrier 16 immediately in front of the obliquely facing hose connector.

Figure 2:
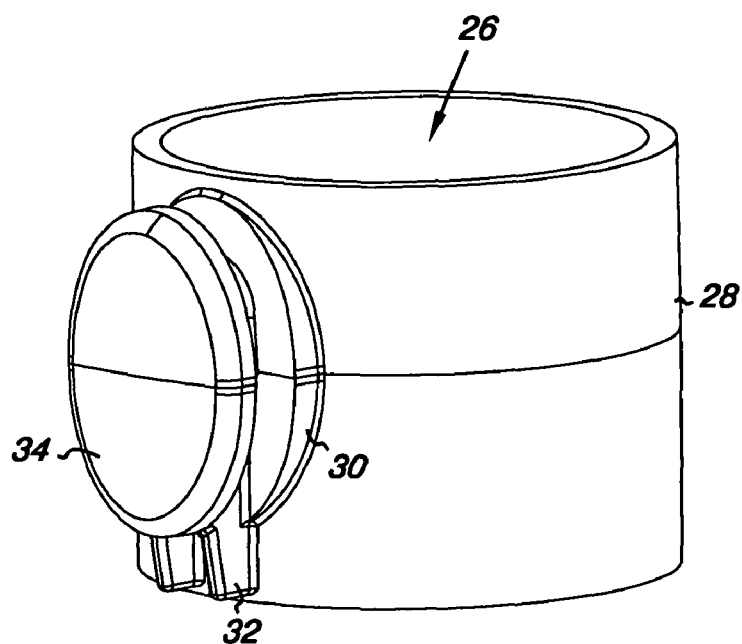
FIGS. 2 and 3 are perspective views of a connector forming part of the nasal mask of FIG. 1.
Figure 3:
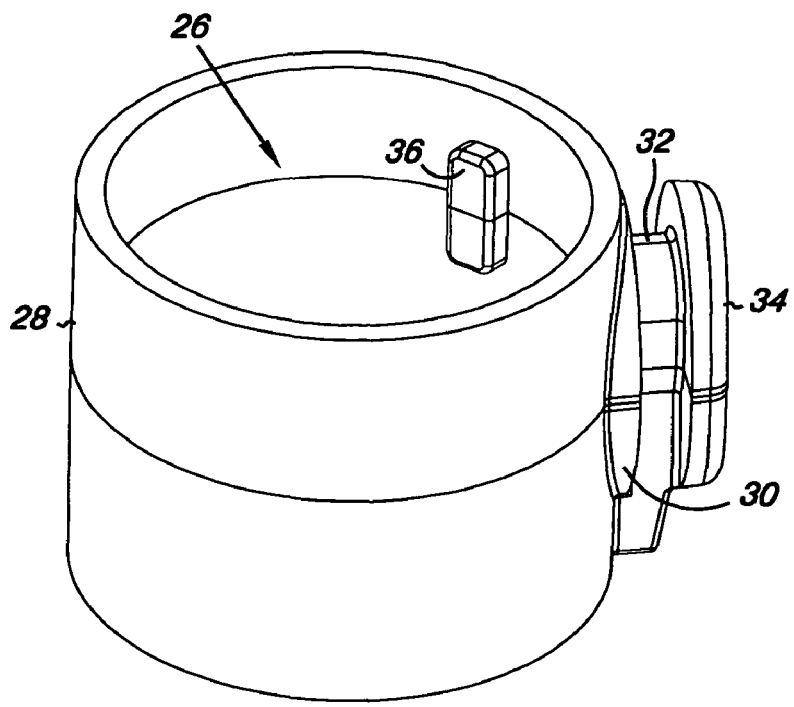

FIGS. 2 and 3 show an orifice 26 surrounded by a thin-walled molded annular socket connector 28 of polymethyl methacrylate, polystyrene, polycarbonate or other rigid plastics material. The connector 28 is located at the top of seal 18 where it joins connector carrier 16 and is typically of external diameter about 20 mm. The inner surface of the connector 28 is formed with a tooth 36 to permit said connector to make a push-and-turn fit with formations on the plug connector which depends from the connector carriage 16. The outer surface of the connector 28 is formed with boss 30 leading via a recessed web region 32 to button 34.

Figure 4:
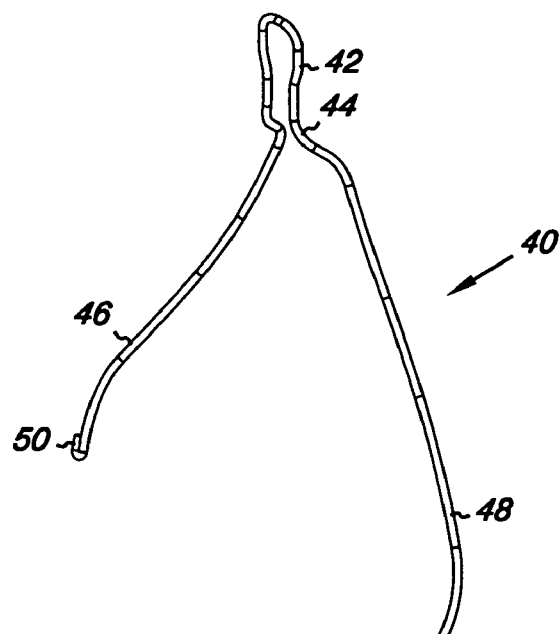
FIG. 4 is a perspective view of a reinforcing wire embedded in the mask of FIG. 1.

A reinforcing wire 40 (FIG. 4) of generally inverted U-shape has an upper relatively narrow loop region 42 for anchoring in load-transmitting relationship over web region 32 between boss 30 and button 34 so that the web region 32 can provide support to reinforcing wire 40 against downward load arising at the nares. The length of the loop region 42, the length of the web region 32 including its downward extension pieces stabilize the position of reinforcing wire 40 against relative movement in a medial-lateral direction and boss 30 and button 34 stabilize it against movement in an anterior-posterior direction. The loop region 42 leads to relatively short divergent transition region 44 which is offset inwardly of the connector 28 or rearwardly relative to the face and in turn leads to relatively long depending limbs 46, 48 that terminate at short regions 50 where the cut ends of limbs 46, 48 are returned. The wire can be of any material that is easily deformable but that retains its shape unless deliberately deformed. The reinforcing wire 40 is preferably of brass or steel, preferably stainless steel which may be nickel-plated. Each side of the wire 40 is of length about 80 mm.

Figure 5:
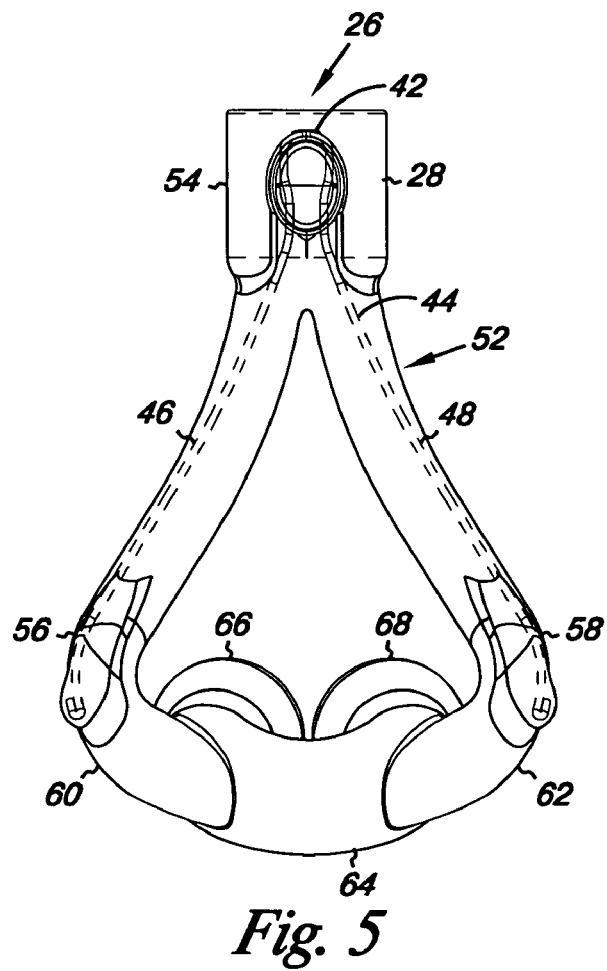
FIG. 5 is a front view of the nares seal with the seal body shown as transparent to reveal the connector and the embedded reinforcing wire.
Figure 6:
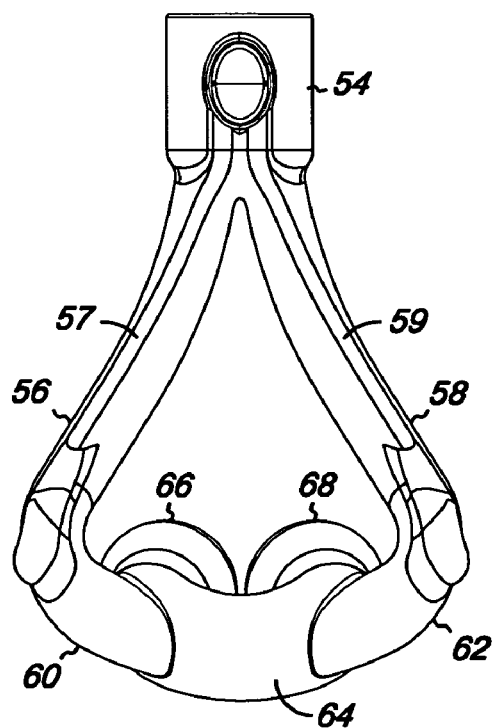
FIG. 6 is a front view as FIG. 5 but with the seal body shown in solid to reveal anterior ribbed pockets in which the reinforcing wires are embedded.
Figure 7:
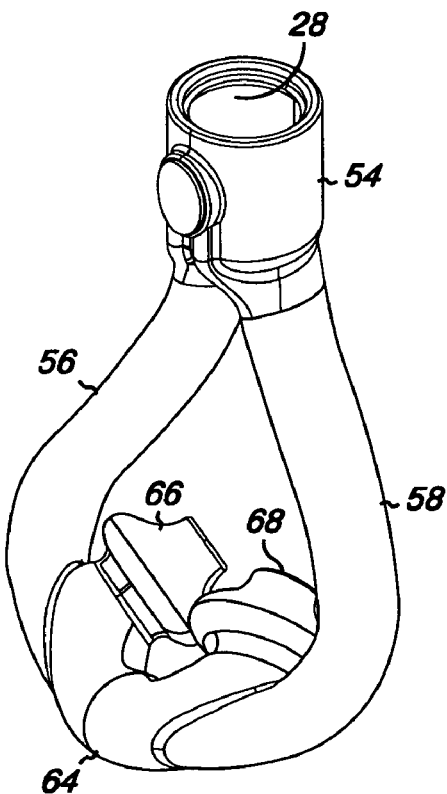
FIG. 7 is a front ¾ view of the nares seal.

In FIG. 5, soft plastic tubing 52 e.g. of medical grade silicone rubber is formed into a triangular shape defining an upper region or space 54 that fits over and surrounds the connector 28. The tubing bifurcates closely below the connector to define two smaller tubes 56, 58 that are laterally spaced and extend downward around the triangular space. Each tube is of generally elliptical or oval profile with an aspect ratio of about 2 and with an anterior-posterior major dimension for an adult patient of typically of about 15 mm and with a transverse minor dimension typically of about 9 mm, the oval shape providing air passages of the required dimensions while being visually relatively unobtrusive. Most preferably, the wire 40 is molded into the outside (front) edges of the tubes 56, 58. The wire 40 provides mild apposing force to hold flanges 74 of the outlet tubes 66,68 (described below) against the nares, so that neither headgear straps nor the mask holder 14 need be in contact with the seal 18. The seal may also be adjusted slightly to accommodate differences in facial topology by bending the wire 40. In the illustrated structure, the depending limbs 46,48 of the reinforcing wire are molded into ribbed pockets 57, 59 which extend along the front of each tube 56, 58 and provide an upstand of about 2-3 mm from the lumen, see FIG. 6 and FIG. 8.

Figure 8:
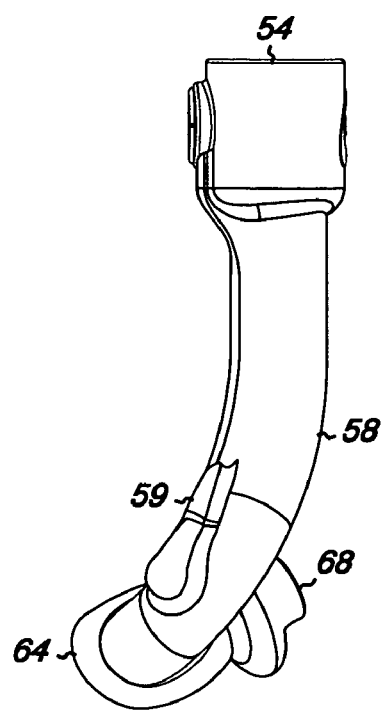
FIG. 8 is a side view.

When viewed in profile as in FIG. 8, the tubes 56, 58 are curved in an anterior direction, with the steepness of curvature increasing progressively with distance from region 54. Below the nose, and below the ends of wire limbs 46, 48, the tubes 56, 58 merge into relatively short transition regions 60, 62 which curve obliquely inwardly and in turn merge into a generally U-shaped lowermost region 64 or collar which is slightly larger than tubes, being approximately 20 mm across. The collar supports a pair of outlet tubes 66, 68 that are directed obliquely rearwardly and upwardly at an angle of about 30° as viewed in FIG. 8 so as to fit into the anterior nares of the patient.

Figure 9:
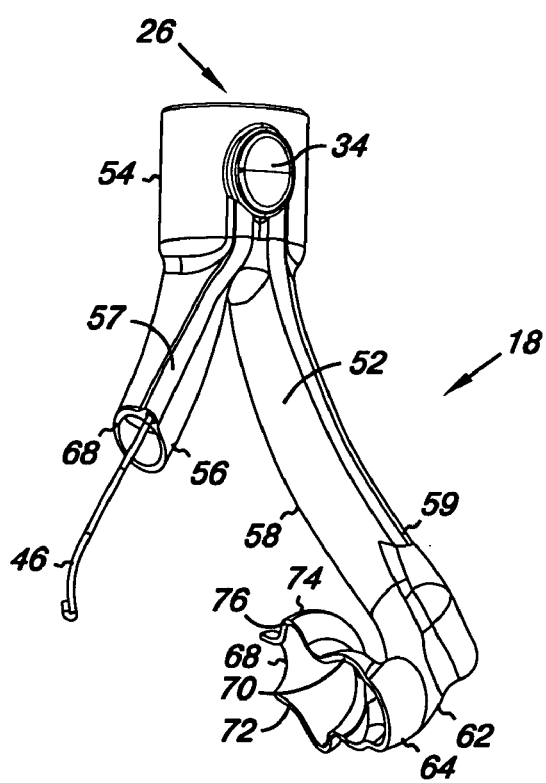
FIG. 9 is a partly cut-away front ¾ view.
Figure 10:
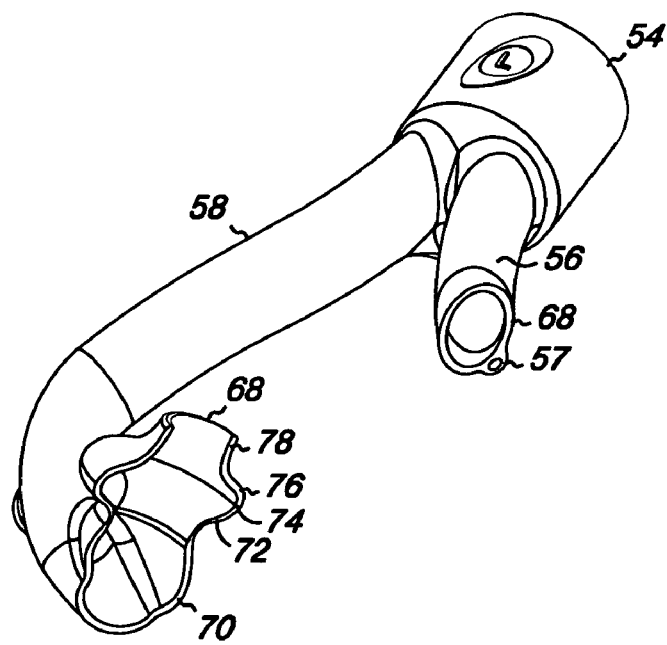
FIG. 10 is a partly cut-away rear ¾ view.

In FIG. 9 the tube 56 is shown cut-away to reveal wire 46 extending from anterior rib 57 and to reveal the oval shape of the tube. Outlet tube 68 is also seen cut-away in FIGS. 9 and 10. It has a relatively thick base region 70 leading to flange 74 that is defined by relatively thin anterior region 72 and thicker posterior region 76. The posterior region 76 flares into reduced diameter distal region 78.

Figure 11:
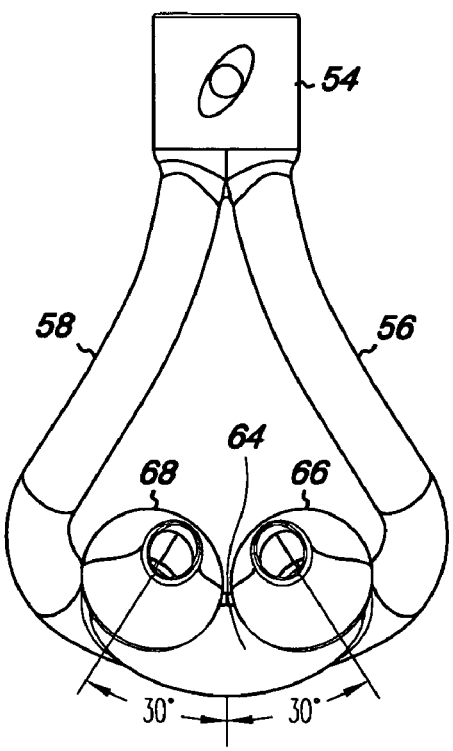
FIG. 11 is a rear view and FIG. 12 is a view from above.

As can be seen in FIG. 11, when viewed from behind the mask, the flanges 74 of the two outlet tubes and the two distal regions 78 are both oval with their longer dimensions making an angle of about 30° with the anterior-posterior direction as shown, the distal regions being about 10 mm by 7 mm. In use, the distal regions 78 become inserted into the anterior nares of the patient, with the flanges 74 acting as seals to prevent air leakage.

Figure 12:
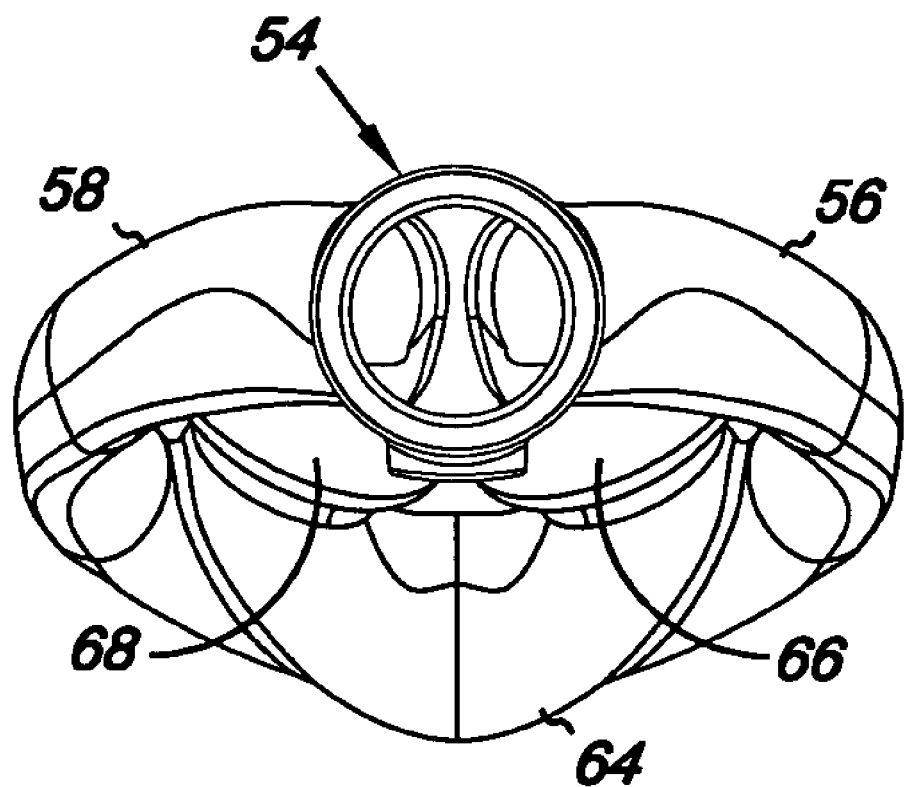

FIG. 12 is a top view of the mask showing the inlet orifice 26 surrounded by the connector 28. The wire support 32 is encircled by the top loop 42 of wire 40 located towards the anterior of the mask. The tubes 56, 58 are seen, as is collar 64, which holds them together at their lower ends. Flanges of outlet tubes 66, 68 also appear.

As explained above, the nares seal 18 is intended to be connected to and to depend from a support maintained by suitable headgear at a stable position above the nose and to be connected to the support by a rigid connector at the top of the seal so that the support can provide a reaction to forces on the mask. In CPAP, air from a blower is supplied to the seal 18 in excess of breathing requirements so that the pressure within the mask is always positive, falling somewhat during inhalation and rising somewhat during exhalation.

The seal is subject to pressure of gas in the nares which produces loads acting obliquely forwardly and downwardly at an angle of about 30°, along the axes of the tubes 66,68. The downward components of these loads are reacted by the connector 28, which is mechanically connected to a depending connector of the plenum. Compressive load between the seal and the nares, and the forward component of the load can deflect the relatively thin deformable region 72 of each outlet tube to facilitate fitting of the mask to the face. The U-shaped collar 64 can react load along the axes of the outlet tubes with relatively little deflection, and the transition regions 62, 64 though also composed of silicone rubber or other deformable material only without reinforcing wires also undergo relatively little deflection. The transition regions apply the load predominantly to wire limbs 46, 48, which stiffen the tubes 56, 58, and the load is reacted at connector 28 at button 34. The combination of the stiffness of the wire support 40 with the stiffness of the silicone rubber or other material of tubes 56, 58 enables the flanges 74 to be held apposed to the anterior nares and to resist displacement from the nares even when the patient exhales strongly. The distal regions 78 remain in position in the nares and are remarkably resistant to displacement from their correct position even on vigorous exhalation intended to produce this result. Despite the construction in flexible materials such as silicone rubber and relatively thin reinforcing wire, embodiments of the present mask can provide an unexpectedly stable interface between the nares and overlying portions of a patient interface.

The body of the seal may be molded in one piece from silicone rubber or other deformable rubber or plastics material, with the reinforcing wire 40 introduced into the mold so that it becomes embedded in the material of the body. The region 64 may be formed with a slotted opening to give access to forming tools during the molding process, the slot being heat-sealed after molding. The connector 28 is then fitted to upper region 54 of the mask body. For that purpose, region 54 as molded is provided with an oval aperture through which button 34 appears. In order to fit the connector 28, the region 54 may be pulled downwardly away from the looped region 42, after which web region 32 is introduced between the uppermost part of limbs 46, 48 and the connector is engaged with region 42 to anchor the top loop 42 of the reinforcing wire. The region 54 is then folded back over the connector 28, after which additional silicone may be coated over the opening in the region 54 to conceal the button 34 and cured.

Various modifications may be made to the mask described above without departing from the invention. For example, the order of plug and socket connection between the connector carrier 16 and the top of the mask may be reversed with the plug portion on the mask, or other forms of mechanical and gas-tight connection may be used. The reinforcing wire or wires may be located elsewhere than the anterior of the laterally spaced tubes, e.g. along the outer sides thereof. The single U-shaped wire 40 could be replaced by individual wires for each tube 56,58 separately attached to connector 28, although this alternative is less preferred. The tubes 56, 58 that fit into the nares need not be provided with flanges and may be plain, although such constructions are less preferred. The seal may be used with headgear other than that shown in FIG. 1 provided that there is a connector held in a stable position closely above the nose to which the seal may be attached.

We claim:
1. A nares seal comprising:
a connector having an air orifice formed therethrough;
first and second laterally spaced delivery tubes connecting with said air orifice and defining between them a generally triangular open space which extends, when in use, downwardly laterally around at least a portion of a nose of a patient and to a point below the nose of said patient, said delivery tubes including transition regions which curve obliquely inward toward one another and under nares of said patient;
first and second nostril tubes connected with said delivery tubes for insertion into the nares of a patient; and wire support for said laterally spaced tubes extending from the connector and attached along at least a portion of the length of the first laterally spaced delivery tube between the connector and the first nostril tube, and attached along at least a portion of the length of the second laterally spaced delivery tube and second nostril tube.

2. The nares seal of claim 1, wherein the connector is molded of rigid plastics material that fits at an upper end of a body defining the first and second laterally spaced delivery tubes, said body comprises a one-piece deformable plastics or rubber material.

3. The nares seal of claim 2, wherein said wire support is a single wire of a generally inverted U-shape, said wire being rigidly attached at an apex of the inverted U to said connector and limbs of the wire support being embedded in the plastics material of said delivery tubes.

4. The nares seal of claim 3, wherein said limbs are embedded at the anterior of said delivery tubes.

5. The nares seal of claim 4, wherein said limbs are embedded in ribs formed along the anterior of said delivery tubes and upstanding therefrom.

6. The nares seal of claim 2, wherein said body is molded of silicone rubber.

7. The nares seal of claim 1, wherein the nostril tubes are flanged partway along their length.

8. The nares seal of claim 7, wherein said flange is bounded by upper and lower generally frustoconical surfaces, the upper frustoconical surfaces providing abutments for limiting entry of said tubes into the anterior nares and leading to reduced diameter distal regions for entry into the nares, and the lower frustoconical surfaces being of lesser thickness than the remainder of the nostril tube, whereby deformation of the nostril tube in use occurs preferentially at said lower flange.

9. The nares seal of claim 7, wherein said nostril tubes are oval with their longer dimensions directed inwardly and forwardly as viewed from above.

10. The nares seal of claim 1, wherein said delivery tubes lead to a generally U-shaped transversely directed collar that in use fits below the nose, said nasal tubes being carried by said collar and facing obliquely rearwardly and upwardly therefrom.

11. Apparatus adapted to fit to the head of a patient for supply of gas to the nose at a positive pressure for treatment of snoring and sleep apnea, said apparatus comprising: headgear for fitting to the head of a patient; a mask support forming part of said headgear and held in use by portions of said headgear in a stable position above the nose of the patient, said mask support including a manifold chamber, a first connector opening above said manifold chamber for attachment of a gas supply line and a second connector depending from said manifold chamber; and a nares seal connected to said second connector by a third connector forming part of a mask and having an air orifice formed therethrough, said seal further comprising first and second laterally spaced delivery tubes connecting with said air orifice and defining between them a generally triangular open space which extends, when in use, downwardly to a point below the nose of a patient, said delivery tubes including a curve in an anterior direction and further including transition regions which curve obliquely inward toward one another and under nares of said patient, first and second nostril tubes connected with said delivery tubes for insertion into the nares of a patient; and wire support for said laterally spaced tubes extending from the connector to about where said tubes curve inwardly and upwardly.

* * * * *